(12) United States Patent
Yoon

(10) Patent No.: US 6,656,226 B2
(45) Date of Patent: Dec. 2, 2003

(54) PLASTIC JACKET FOR A CEMENTLESS ARTIFICIAL JOINT STEM AND ARTIFICIAL JOINT HAVING THE JACKET

(75) Inventor: Yong-San Yoon, Taejon (KR)

(73) Assignee: Korea Advanced Institute of Science and Technology (KR)

( * ) Notice: Subject to any disclaimer, the term of this patent is extended or adjusted under 35 U.S.C. 154(b) by 0 days.

(21) Appl. No.: 09/779,518

(22) Filed: Feb. 9, 2001

(65) Prior Publication Data

US 2001/0014829 A1 Aug. 16, 2001

(30) Foreign Application Priority Data

Feb. 16, 2000 (KR) .......................................... 2000-7364

(51) Int. Cl.[7] .................................................. A61F 2/36
(52) U.S. Cl. ................................ 623/23.23; 623/23.46; 623/22.4
(58) Field of Search ........................ 623/23.46, 23.52, 623/16.11, 18.11, 23.15, 23.23–23.31, 22.4–22.42, 23.6

(56) References Cited

U.S. PATENT DOCUMENTS

| | | | | |
|---|---|---|---|---|
| 4,790,852 A | * | 12/1988 | Noiles | 623/18 |
| 4,846,839 A | * | 7/1989 | Noiles | 623/18 |
| 4,936,859 A | * | 6/1990 | Morscher et al. | 623/18 |
| 5,409,492 A | * | 4/1995 | Jones et al. | 606/86 |
| 5,702,443 A | | 12/1997 | Brånemark | 623/11 |
| 5,702,445 A | | 12/1997 | Brånemark | 623/11 |
| 6,139,584 A | * | 10/2000 | Ochoa et al. | 623/23.46 |
| 6,156,070 A | * | 12/2000 | Incavo et al. | 623/23.52 |
| 6,168,626 B1 | | 1/2001 | Hyon et al. | 623/18.11 |
| 6,179,877 B1 | * | 1/2001 | Burke | 623/22.12 |
| 6,214,053 B1 | * | 4/2001 | Ling et al. | 623/23.11 |

FOREIGN PATENT DOCUMENTS

DE 19605735 A1 * 6/1997 ............. A61F/2/30

OTHER PUBLICATIONS

DE 19605735–A1; Jun. 1997, Kumm; Translation.*
DE 19605735–A1; Jun. 1997, Kumm; Derwent Abstract.*
Fried, J. R.; "Polymer Science and Technology"; 1995; Prentice Hall PTR; pp. 1, 294–298.*

* cited by examiner

Primary Examiner—Corrine McDermott
Assistant Examiner—Urmi Chattopadhyay
(74) Attorney, Agent, or Firm—Bacon & Thomas, PLLC

(57) ABSTRACT

A plastic jacket for affixing an artificial joint to a bone. The plastic jacket includes a body for contacting with the bone, an opening for receiving the artificial joint, which is formed with a predetermined shape at one end of the body, and an closed wall formed at another end of the body.

2 Claims, 5 Drawing Sheets

PLASTIC JACKET FOR A CEMENTLESS ARTIFICIAL JOINT STEM AND ARTIFICIAL JOINT HAVING THE JACKET

THE BACKGROUND OF THE INVENTION

1. Field of the Invention

The present invention relates to a plastic jacket for a cementless artificial joint stem, and particularly to a plastic jacket for a cementless artificial joint stem, with jacket secured to the bone in such a manner that the cementless artificial joint stem can slide relative to the bone and the plastic jacket enclosing its stem.

2. Description of the Prior Art

Generally, an artificial hip joint, for example, consists of an acetabular part and a femoral or thigh bone part, wherein the acetabular and femoral parts are made of either metal, plastic, or ceramic, independently.

The human femur is formed of the soft cancellous bone in the metaphyseal region and hard cortical bone in the diaphyseal region. Therefore, in order to insert an artificial joint into the human body, operation is performed in such a way that the bone canal is reamed out at the proximal site, the stem of artificial joint is inserted and finally the anchorage is conducted by using cement, or in other case of not using cement, a stem having a porous or roughened surface layer on the outer circumference is inserted so as to allow the surface to get physiological interlocking with the bone as it grows.

The art for surgical operation based on the artificial joint using cement out of the two methods as described above is disclosed in the Korean patent publication 1814/1985 to the present applications as the patentee, titled "Torsion resistant artificial hip joint".

Referring to FIG. 1, the art published in the Korean patent publication is briefly reviewed as below.

FIG. 1 shows the perspective view of an artificial joint using cement according to the conventional art. As shown in the drawing, the artificial joint 1 is integrally composed of a head 2, neck 3, collar 4 and stem 5, starting with the top. The leading end of the collar 4 is curved to be secured tightly in the inner top edge of the cortex of the femur. The stem 5 is in a curved column with the top cross section resembling an ellipse which gradually varies to a circle at the bottom. Such a shape of the stem 5 is intended for protection from rotating due to the compressive force applied vertically from the top of the joint and the lateral force applied in perpendicular direction to the stem 5 of joint at the head 2.

Further, on the upper external surface of such a stem 5 a blade 7 with an appropriate thickness is provided protrusively in longitudinal direction to prevent the joint from turning in the femur even in the case of a torque generated in an arbitrary direction after a surgery, wherein a fixing hole 8 is formed in the center of the blade 7.

On the inward side of blade 7, the stem 5 is formed with a number of lateral grooves at certain longitudinal intervals, in which grooves iron wires 9 in chain form are inserted in a manner of wrapping the stem 5. On the surface of the stem 5 including the surface with chain-like wires 9, cement 6 is coated to a certain thickness. Such a process of pre-coating with cement 6 is to facilitate adhesion with the cement used in the surgical operation and to reduce the heat generated during curing period through the reduced use of cement.

In order to introduce such an artificial joint in a human long bone, reaming is carried out at the bone canal beforehand so that the artificial joint 1 may be inserted with the stem 5, after appropriate amount of cement is injected thereto. Subsequently, the stem 5 is inserted in the cement-injected area, so that this cement may adhere with the pre-coated cement layer 6 on the surface of the stem 5, with the result that the stem 5 can be firmly secured in the femur.

However, the artificial joint using the cement as described above has the drawback in that the connection region is weak due to the fragile cement connection between the joint stem and the bone canal.

In order to compensate for such a drawback, the connection between the femur and the joint stem was modified so as to be physiologically interlocked at the joint stem with the ingrowth or ongrowth of the bone into the porous surface of the stem.

FIG. 2 shows a partially cut-out front view of an artificial joint without using cement according to a conventional art. As shown in the drawing, the artificial joint 10 has a metallic stem 11 coated with a porous plastic 12, the surface of which is porous. Therefore, if the artificial joint coated with the porous plastic is inserted into the bone canal, as mentioned before, then, with gradual in-growth of the femur, the bone physiologically gets interlocked with the surface layer of the porous plastic 12 so as to fix the metallic stem 11 to the bone.

In the course of use of such cementless artificial joint which is fixed to a bone in a physiological manner, the axial force applied to the head 2 of a joint stem acts as a shear force at the interface of the bone and the stem to cause a micro sliding movement between the bone and the porous plastic 12. Owing to resulting stress concentration, the porous plastic 12 attached to the surface of the stem is separated from the bone to make a gap between the stem and the bone, into which gap wear particles are infiltrated to accelerate osteolysis.

SUMMARY OF THE INVENTION

Therefore, the present invention was created to resolve the problem with the conventional art as described above and the object of the present invention is to provide a plastic jacket for a cementless artificial joint stem, wherein shear force detrimental to the service life of an artificial joint can be markedly reduced, by constructing the plastic jacket so as to be fixed to the bone and simultaneously to enclose the surface of the stem to thereby allow for the stem of the artificial joint to slide vertically relative to the bone, and wherein osteolysis of a bone due to the infiltration of wear particles can be minimized by curbing the gap formation between the bone and the stem.

Further, another object of the present invention is to provide a cementless artificial joint in which a stem is covered by a plastic jacket for the artificial stem.

To achieve the above first object, there is provided, according to an aspect of the invention, a plastic jacket for cementless artificial joint stem that is made of plastic and is so formed as to enclose at least a part of the stem of the cementless artificial joint, the stem and jacket being inserted longitudinally in the opening formed in the bone of a human body, and the plastic jacket has roughened surfaces so that the bone can interlock with the plastic jacket as the bone grows onto the porous surface.

To achieve the above-described second object of the invention, according to another aspect of the invention, there is provided an artificial joint with a plastic jacket for a cementless artificial joint stem, which has a head, neck and stem so as to be inserted in an opening formed by reaming out some part of the bone canal in a human body, wherein the plastic jacket is formed that it may enclose at least a part of its stem and is made of plastic, the surface of which characteristically is porous or roughened so that the bone can easily get interlocked by in-growth of the bone into the porous surface of the plastic jacket and wherein the end part of the jacket encompasses a redundant space to allow for the stem to slide down.

In the case of using an artificial joint equipped with a plastic jacket for a stem according to the invention, shearing stress is drastically reduced and proper amount of compressive stress is instead secured at the interface between the bone and the plastic jacket to prevent the sliding movement at that interface and simultaneously to suppress the formation of a gap between the plastic jacket and the bone, so that the osteolysis of femur due to the infiltration of wear particles can be minimized.

Further, in the case of using an artificial joint equipped with a plastic jacket for a cementless artificial joint stem according to the invention, the vertical load is partly converted into a hoop stress, which includes strain large enough to physiologically activate the bone (Wolfe's law) even at the proximal region of the femur bone, alleviating the phenomena of stress shielding drastically.

Furthermore, the plastic jacket for a cementless artificial joint stem according to the invention has a porous or roughened surface for easy physiological interlocking of the jacket with the bone, and on the other hand, the part in contact with the bone consists of plastic, so that it can be separated easily from the bone to minimize the damage on the bone, when its removal is required.

DESCRIPTION OF A PREFERRED EMBODIMENT

A preferred embodiment of a plastic jacket for a cementless artificial joint stem and an artificial joint equipped with that plastic jacket will be described in detail below by referring to accompanying drawings.

Figure 1:
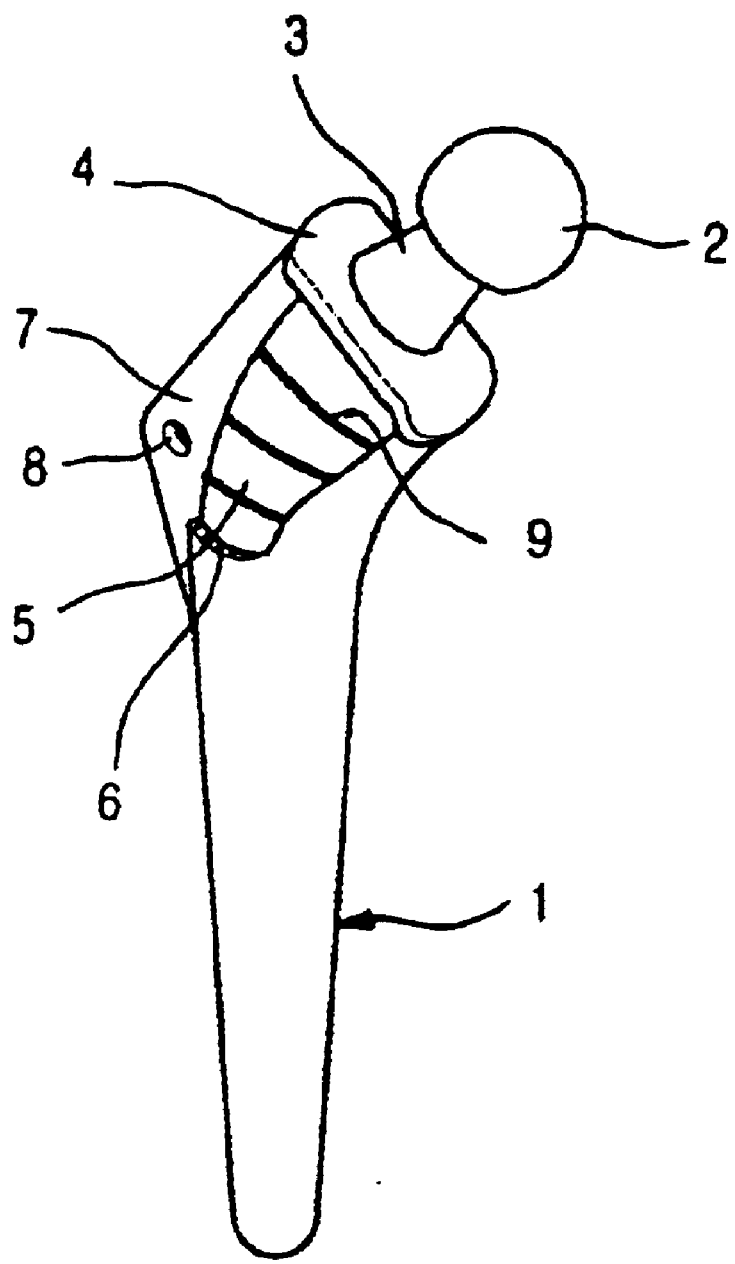
FIG. 1 shows the perspective view of an artificial joint using cement according to a conventional art.
Figure 2:
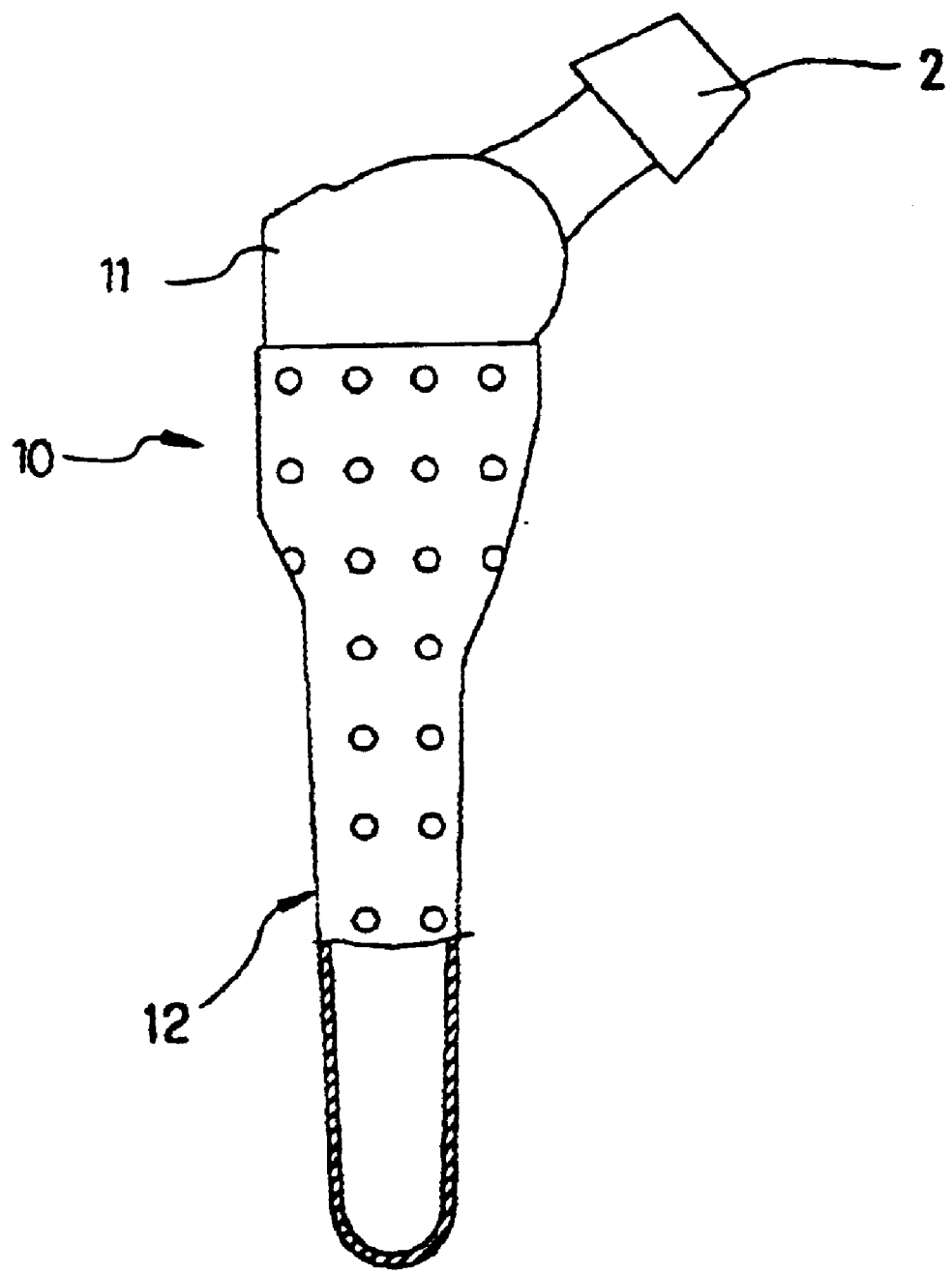
FIG. 2 shows a partially cut-out front view of an artificial joint without using cement according to a conventional art.
Figure 3:
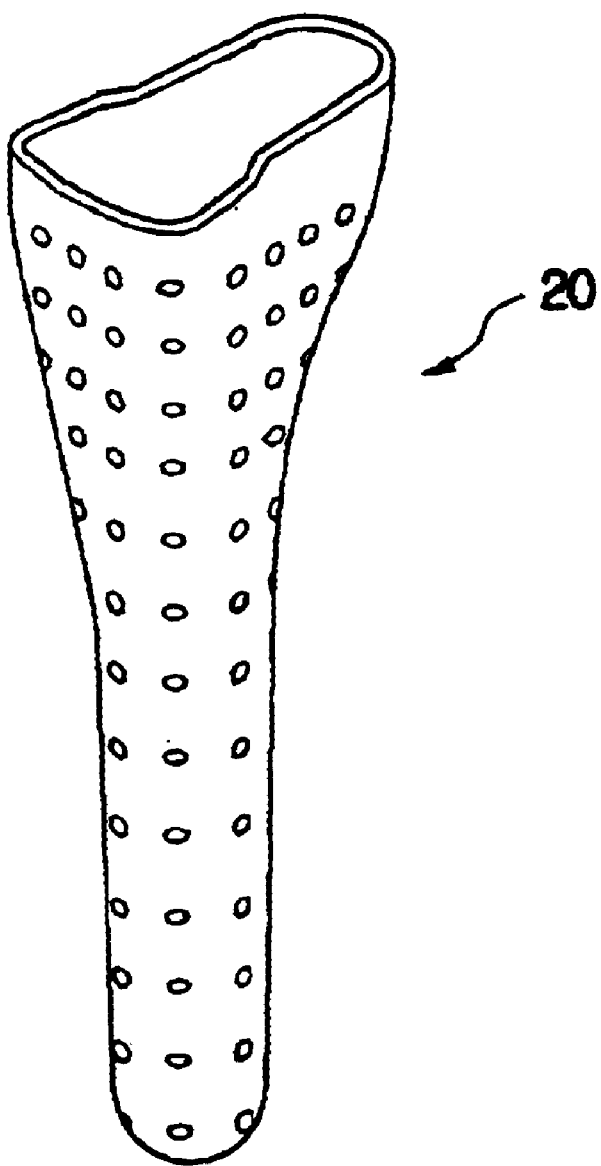
FIG. 3 shows a plastic jacket for a cementless artificial joint stem according to an embodiment of the present invention.

As can be seen in FIG. 3, the plastic jacket 20 for a cementless artificial joint stem according to a preferred embodiment of the invention is in the form adapted for enclosing the stem of the cementless artificial joint when the stem is inserted, or in the form of a bag. The plastic jacket 20 is so formed that the stem may slide down vertically in the jacket when it is inserted thereinto and dimensioned in its diameter to match the outer diameter of the stem.

In addition, the plastic jacket 20 is formed a little longer than the stem so that a predetermined space between the lower end of the stem and the lower end of the plastic jacket remains to prevent the lower tip of the stem from touching the lower end of the plastic jacket 20 when the stem is placed in the plastic jacket. The formation of such a prescribed space is to prevent a damage on the plastic jacket 20, if the stem sinks downward.

Further, the plastic jacket 20 is generally made of plastic, wherein the outer surface of the plastic jacket is porous or rough. The reason for the formation of such irregularities on the surface of the plastic jacket 20 is to make it be easy that the bone interlocks with the plastic jacket surface with the in-growth of the bone.

Now, the procedure of inserting a plastic artificial joint into the plastic jacket mentioned above will be described as below.

Figure 4:
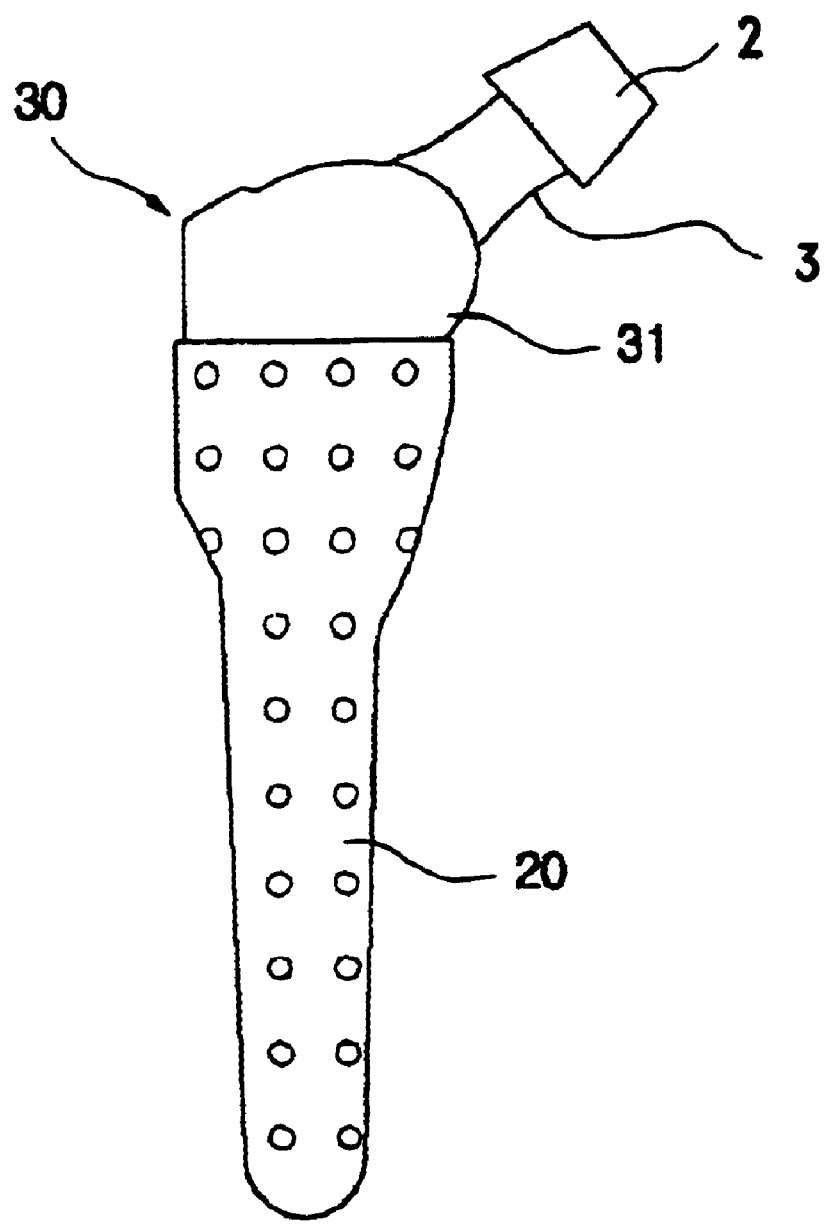
FIG. 4 shows a cementless artificial joint stem as inserted in the jacket shown in FIG. 3.

As can be seen from FIG. 4, the stem 31 of an artificial joint 30, the surface of which stem is previously polished, is first inserted into a plastic jacket 20 according to the invention. Then, a prescribed space between the lower end of a stem 31 and the lower end of a plastic jacket 20 is formed, so that the stem 31 can slide down relative to the plastic jacket 20, as mentioned earlier.

Figure 5:
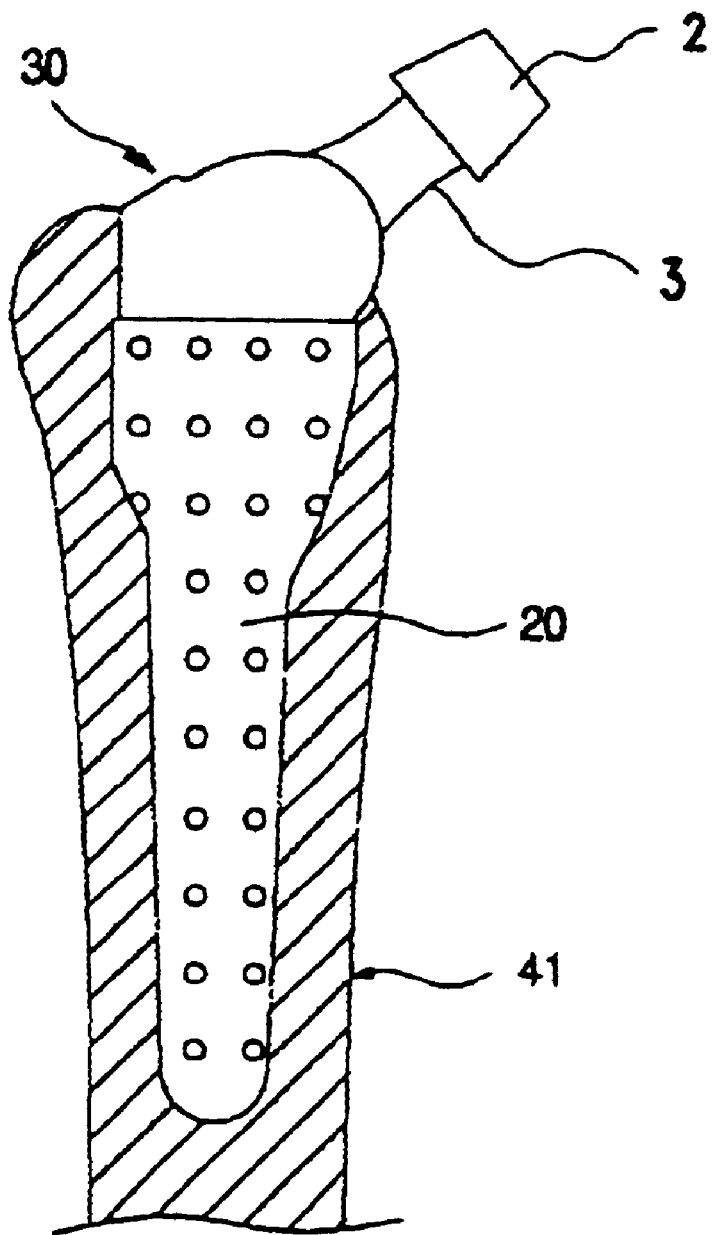
FIG. 5 shows an artificial joint shown in FIG. 4 as inserted in the bone in a human body.

Now, the artificial joint 30, wherein the plastic jacket 20 is placed over a stem 31, is to be inserted into the bone canal in a human body. To that end, the bone canal is reamed to form an opening, so that the plastic jacket 20 in which the stem 31 of artificial joint 30 is placed may be inserted into the opening, and thus the artificial joint 30 housed in a plastic jacket 20 is inserted thereinto, as seen in FIG. 5. Then, the plastic jacket 20 having a porous or roughened surface gets interlocked physiologically with the bone 41, as the bone 41 makes in-growth onto the porous plastic jacket surface. Consequently, the bone 41 and the plastic jacket 20 are stoutly combined, while the stem 31 can slide down in relation to the plastic jacket 20.

The plastic jacket according to the present invention can be applied to all kinds of artificial joint including the hip joint, knee joint, shoulder joint and the like.

It is to be understood that, while the invention was described only with respect to a preferred embodiment of a plastic jacket for cementless artificial joint stem and an artificial joint having the same jacket, the invention is never restricted to that embodiment and a variety of modifications and alterations would be possible to a man skilled in the art by referring to the description or drawings presented here and within the spirit of the invention and thus those modifications or alterations are to fall within the scope of the invention, which scope should be limited only by the attached claims.

What is claimed is:

1. An artificial joint adapted for pivotally connecting a first bone to a second bone, wherein a hole is formed in the second bone, the artificial joint comprising:

a head adapted for connecting with the first bone;

a stem having a longitudinal length and adapted to fit into the hole of the second bone;

a neck connecting the head to the stem;

a jacket enclosing the stem, the jacket comprising an outer surface and a porous body, the body configured to be inserted into the hole of the second bone so that substantially all of the outer surface of the jacket is in direct contact with inner walls of the second bone formed by the hole thereof, the jacket comprising a blind opening that receives most of the stem;

a gap formed between the stem and a lower portion of the jacket so that the stem can slide partially along the longitudinal length of the stem in the gap; and the body of the jacket comprises a plastic material, and the outer surface of the body is rough, such that the jacket is adapted to adhere to the second bone by natural growth of the second bone onto the outer surface of the jacket without use of cement between the outer surface of the jacket and the inner walls of the second bone.

2. A method for pivotally connecting a first bone to a second bone having a hole, the method comprising:

providing an artificial joint comprising a head adapted for connecting with the first bone, a stem having a longitudinal length and adapted to fit into the hole of the second bone, a neck connecting the head to the stem, and a jacket enclosing the stem, the jacket comprising an outer surface, a porous body and a blind opening that receives most of the stem, the body of the jacket comprises a plastic material, and the outer surface of the body is rough, and a gap is formed between the stem and a lower portion of the jacket so that the stem can slide partially along the longitudinal length of the stem in the gap;

pivotally connecting the head to the first bone;

inserting the jacket enclosing most of the stem into the hole of the second bone so that substantially all of the outer surface of the jacket is in direct contact with inner walls of the second bone formed by the hole thereof; and permitting natural growth of the second bone onto the outer surface of the jacket without use of cement between the outer surface of the jacket and the inner walls of the second bone in order to adhere the second bone to the jacket.

* * * * *